United States Patent
Colak

[19]
[11] Patent Number: 5,903,357
[45] Date of Patent: May 11, 1999

[54] METHOD AND APPARATUS FOR IMAGING AN INTERIOR OF A TURBID MEDIUM

[75] Inventor: Sel B. Colak, Eindhoven, Netherlands

[73] Assignee: U.S. Philips Corporation, New York, N.Y.

[21] Appl. No.: 08/980,756

[22] Filed: Dec. 1, 1997

[51] Int. Cl.⁶ .................................................. G01N 21/00
[52] U.S. Cl. ................................................................ 356/432
[58] Field of Search ..................................... 356/432, 337, 356/446, 332–343; 250/341.1, 340, 341.7, 332, 358, 339, 341; 128/633, 634, 664, 665, 653.1; 600/473–476

[56] References Cited

U.S. PATENT DOCUMENTS

| | | | |
|---|---|---|---|
| 4,030,828 | 6/1977 | Sonobe et al. | 356/96 |
| 4,515,165 | 5/1985 | Carroll | 128/664 |
| 5,349,951 | 9/1994 | Ito et al. | 128/633 |
| 5,625,458 | 4/1997 | Alfano et al. | 356/446 |
| 5,694,938 | 12/1997 | Feng et al. | 128/664 |
| 5,719,398 | 2/1998 | Colak | 250/341.1 |

*Primary Examiner*—Frank G. Font
*Assistant Examiner*—Michael P. Stafira
*Attorney, Agent, or Firm*—Dwight H. Renfrew, Jr.

[57] ABSTRACT

A method of imaging an interior of a turbid medium, for example a part of a breast of a human female, the turbid medium is irradiated with light and measurement of the intensity of light propagated along a plurality of light paths through the turbid medium is measured. An image of the interior of the turbid medium is reconstructed from the intensities measured. Furthermore, possible strengths assignable to each pixel of the image are determined from combinations of weighting functions and differences between expected photon fluences and a measured photon fluences from the intensities measured. A distribution function is made up from the possible strength determined. In a last step the image is determined from the distribution function. Further steps can be carried out to correct for objects of high strength in the image.

12 Claims, 6 Drawing Sheets

METHOD AND APPARATUS FOR IMAGING AN INTERIOR OF A TURBID MEDIUM

BACKGROUND OF THE INVENTION

1. Field of the Invention

The invention relates to a method of imaging an interior of a turbid medium, including consecutive irradiation of the turbid medium with light and measurement of the light propagated along a plurality of light paths through the turbid medium, and determination of an image of the interior of the turbid medium from the intensities measured. The invention also relates to a device for carrying out such a method.

2. Description of the Related Art

In the context of the present Patent Application light has to be understood as electromagnetic radiation having a wavelength in the visible or infra-red range approximately between 400 and 1000 nm. Furthermore, a turbid medium has to be understood as a volume of a highly scattering substance, for example, an Intralipid solution or biological tissue.

Such a method is known from the article "Back-projection Reconstruction of Cylindrical inhomogeneities from Frequency Domain Optical Measurements in Turbid Media", S. A. Walker et al, OSA Topics on Advances in Optical Imaging and Photon Migration, 1996. In the cited article, the known method is used for the imaging of a turbid medium having optical properties similar to those of biological tissue. In medical diagnostics the known method and device could be used for imaging the internal structure of breast tissue of a human female. For example, a tumor can be localized in such an image of the internal structure of breast tissue. The known method employs a back-projection method similar to X-ray computer tomography to obtain an image of the region of interest inside the turbid medium from physical parameters of the measured intensities. In said back-projection method, the physical parameters are calculated from frequency domain data. Furthermore, a value of the optical absorption coefficient $\mu_\alpha$ and a value of the reduced scattering coefficient $\mu'_s$ are used as reconstruction parameters. Said values are calculated for each measurement and, in a single step, are projected back along the region between source and detector while employing an appropriate weighting function. An image is formed by averaging data from multiple source detector scans taken at multiple angles. A weighting function can also be chosen in order to maximize resolution which weighting function consists of an evenly weighted straight line between source and detector multiplied by a filtering function. That filtering function accounts for the size of the sampling interval. A drawback of the known method is that the known method is not capable of reconstructing inhomogeneities beyond a source detector line.

It is an object of the invention to provide an image reconstruction algorithm for imaging inhomogeneities also beyond the source detector line. It is a further object to provide a real-time imaging technique for use in medical imaging processes, for example mammography. Therefore, the method according to the invention is characterized in that it includes the following steps:

c) determination for each measurement of a difference between an expected photon fluence and a measured photon fluence from the intensity measured, d) determination of possible strengths assignable to each pixel of the image from combinations of weighting functions and the differences determined, e) determination of a distribution function of the possible strengths assignable to each pixel, f) determination of an image from the distribution function determined.

In the present Patent Application the expected photon fluence is defined as $$\phi_0(r_d) = \frac{S_o}{4\pi D'} \cdot \frac{\exp[-K|r_d - r_s|]}{|r_d - r_s|}$$

in which $S_O$ represents the source intensity, $K=(\mu_\alpha c/D')^{1/2} \sim (3\mu_\alpha \mu'_s)^{1/2}$, $D'=cD=c/[3(\mu'_s+\mu_\alpha)]$ is the photon diffusion coefficient (in m²/s) and c is the speed of light in the turbid medium (in m/s). Furthermore, the strength q of an inhomogeneity at a position r can be regarded as the effect on the measured intensity of the light an is given by the formula $$q(r) = \frac{1}{P(r_s, r_d, r)} \cdot \frac{\phi_0(r_d) - \phi(r_d)}{\phi_0(r_d)},$$

wherein $$P(r_s, r_d, r_l) = \frac{\exp[-K(|r_l - r_s| + |r_l - r_d| - |r_d - r_s|])}{|r_l - r_s||r_l - r_d|/|r_d - r_s|}$$

and $r_l, r_s, r_d$ represent position vectors of a point in the object space, a light source position, and a detector position, respectively and $\phi(r_d)$ is the measured photon density.

Furthermore, a weighting function is defined as a function giving a dependency of the strength of an object of a position r, which strength introduces a normalized intensity change at a detector position $r_d$ in light from a source at position $r_s$. The weighting function W is defined as the inverse function of the perturbation function P, so $$W = \frac{1}{P}.$$

The distribution function is defined as a function giving a correlation between the possible strengths assignable to each pixel of the reconstructed image for the differences determined.

The effect of said steps is that an image is reconstructed containing an non-blurred image of a strong object. The invention is based on the insight that the possible strengths assignable to a pixel can be derived from a combination of the weighting function and the differences between the measured photon fluence and an expected photon fluence for each light source position and each detector position and that furthermore the possible strengths determined for different light source positions and detector positions must correlate in order to assign a value of the strength to that pixel. Said correlation can be determined by employing the distribution function. Consequently, determination of an image from the distribution function can be performed by employing statistics from the distribution function. Furthermore, said method enables three-dimensional imaging because the reconstruction of an image is not limited to inhomogeneities in a source detector plane only, but because of the use of the weighting function, also accounts for inhomogenities beyond the source detector plane.

A further advantage of the method is that fewer measurements of different source detector positions are suffice as compared to the known back-projection method.

An embodiment of the method according to the invention is characterized in that the method also includes the following steps:

determining intensities due to a perturbation function for the position of a strong object, subtracting the intensities determined from the intensities measured, repeating the steps c) to f).

The perturbation function $P(r_l, r_s, r_d)$ is defined as the inverse function of the weighting function. The intensity at a detector position is then given by $I = A_O \Phi(r_d) = A_O \Phi_O(r_d)[1 - qP(r_l, r_s, r_d)]$, wherein $A_O$ (in cm$^2$) a collection area of the input window f the detector, q represents the strength of the perturbation and $\Phi_{O(rd)}$ is defined as $$\frac{S_o}{4\pi D} \frac{\exp[-K|r_d - r_s|]}{|r_d - r_s|}$$

in which $S_O$ represents the initial source intensity and $$D = \frac{1}{3(\mu'_s + \mu_a)}$$

represents the normalized photon diffusion coefficient. A strong object is an indication for an inhomogeneity having a large value of q. A small object is an indication for an inhomogeneity with a small value of q.

Subtracting the effect of the strong object from the intensities measured and repeating said steps of the image reconstruction process produces an image in which smal objects are deblurred. Furthermore, the image can be refined, by a small number of these iterations, so that in the resultant image more smal objects become visible.

An embodiment of the method according to the invention is characterized in that the distribution function comprises a histogram for each pixel, in which histograms each bin represents a value of the possible strength and the frequency of the bin represents the occurrence of the possible strengths determined. An image of the interior of the turbid medium is then formed by using the statistical information of said histogram. Generally speaking, a high frequency indicates an inhomogeneity for that pixel in the turbid medium. Statistical parameters that may used for forming the image are, for example, maximum value or peak value, mean, variance and standard deviation.

An embodiment of the method according to the invention is characterized in that for each pixel the value of the bin belonging to maximum frequency of the histogram of the pixel is assigned to the pixel. The effect of this step is that the possible strength of the pixel on which the different possible assignable strengths agree or correlate is assigned to the pixel.

An embodiment of the method according to the invention is characterized in that for each pixel the pixel value assigned is multiplied by a correction factor $$\frac{1}{1 + a\sigma_k},$$

wherein $\sigma_k$ is the standard deviation of the histogram of the pixel and a is a constant determined by the desired bit accuracy of the image as $$a = \frac{2^b}{q_{max}},$$

wherein b represents the bit accuracy and $q_{max}$ is the maximum value of the weighting function. Bit accuracy is defined as the number of binary digits representing the maximum possible values of a pixel in the image. The effect of this step is that the strength of the pixel is corrected for the standard deviation of the histogram. For a high standard deviation $\sigma_k$ only a small value of the strength will be assigned to the pixel. For a low standard deviation $\sigma_k$ the histogram is peaked around a central value and that central value will be assigned to the pixel.

The invention also relates to a device, which is provided with a) a light source for irradiating the turbid medium, b) a plurality of detectors for measuring light intensities of light propagated through the turbid medium at a plurality of different positions, c) means for irradiating the turbid medium from a plurality of different positions connected to the light source, d) means for selecting a detector from the plurality of detectors, e) a control unit for generating control signals for the means for controlling the means for irradiating the turbid medium and the means for selecting detectors, and f) a reconstruction unit for reconstructing an image from the measured intensities, the reconstruction unit also being arranged to carry out the following steps:

1) consecutive irradiation of the turbid medium with light and detection of the light propagated along different light paths through the turbid medium, 2) determination of an image of the interior of the turbid medium from the measured intensities, characterized in that the reconstruction unit is further arranged to carry out the following sub-steps for determining the image of the object:

3) determination, for each measurement, of a difference between an expected photon fluence and a measured photon fluence from the intensity measured, 4) determination of possible strengths assignable to each pixel of the image from combinations of weighting functions and the differences determined, 5) determination of a distribution function of the possible strengths assignable to each pixel, 6) determination of an image from the distribution function determined.

The above and other, more detailed aspects of the invention will be explained hereinafter by way of example with reference to the drawing.

DETAILED DESCRIPTION OF THE PREFERRED EMBODIMENTS

Figure 1:
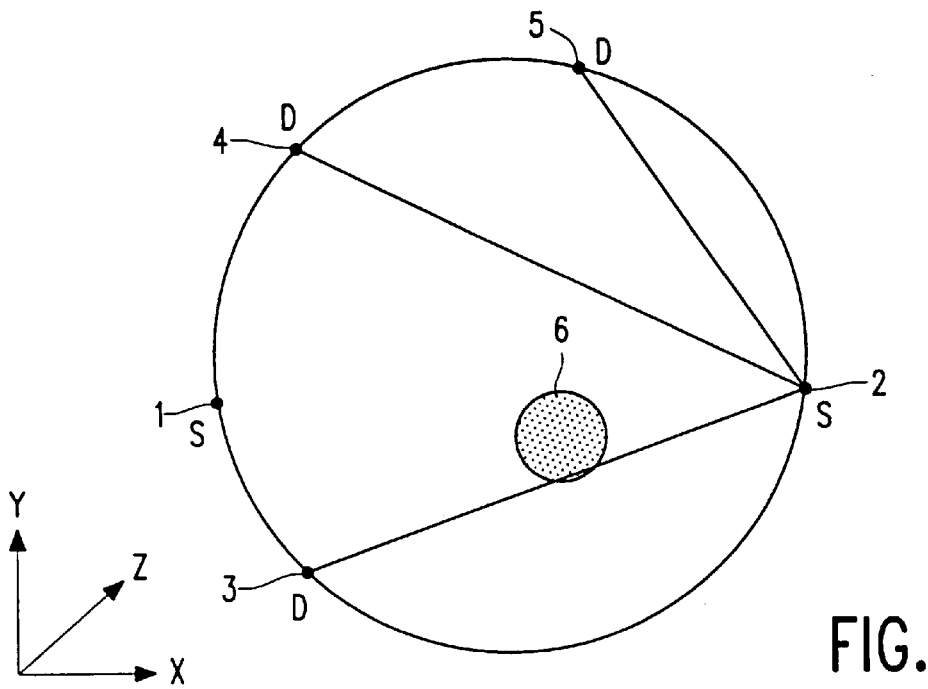
FIG. 1 shows a circular configuration of light sources and detectors.

The general principles of the invention will be elucidated with reference to FIGS. 1–7. FIG. 1 shows a circular configuration of light sources and detectors. In FIG. 1. light sources 1,2 and detectors 3,4,5 are located on a circle around a turbid medium, for example, an Intralipid solution or biological tissue. The diameter of the circle is, for example, 100 mm. In the Intralipid solution an inhomogeneity 6, for example an absorbing cylinder of a synthetic material is immersed. The diameter of the absorbing cylinder 6 is, for example 10 mm. The positions of the sources, detectors and objects are given with respect to an orthogonal coordinate system x,y,z in which $r_s=(x_s,y_s,z_s)$, $r_d=(x_d,y_d,z_d)$, $r_l=(x_l,y_l,z_l)$ are the positions of the source, the detector and an object, respectively. In FIG. 1 the sources and detector are drawn in the x-y plane of the coordinate system.

A diffusion equation is used to describe the transport of light in the turbid medium. Solution of the diffusion equation in a homogeneous medium with a time invariant source $S_O(1/s)$, located at $r_s$, yields the photon density at a general position r, where $$\phi_0(r) = \frac{S_0}{4\pi D'} \frac{\exp[-K|r-r_s|]}{|r-r_s|} \tag{1}$$

Therein, $K=(\mu_\alpha c/D')^{1/2} \sim (3\mu_\alpha \mu'_s)^{1/2}$, $D'=cD=c/[3(\mu'_s+\mu_\alpha)]$ is the photon diffusion coefficient (in $m^2/s$) and c is the speed of light in the turbid medium(in m/s). The photon fluence rate $\Phi(r)(1/cm^2\text{-sec})$ resulting from this photon density is $$\Phi(r) = \frac{S_0}{4\pi D} \frac{\exp[-K|r-r_s|]}{|r-r_s|} \tag{2}$$

If a collection area $A_O(cm^2)$ is assumed at an output window of a source, and any corrections due to the detector input window are ignored, the output intensity, $I_{out}$ (photons/sec) is given by $$I_{out}(r) = A_0 \Phi_0(r) \frac{S_0 A_0}{4\pi D'} \frac{\exp[-K|r-r_s|]}{|r-r_s|} \tag{3}$$

In order to probe the turbid medium, measurements are performed at a detector position $r_d$, and the output of the detector is obtained as a result of the propagation of light from a source at a position $r_s$. A perturbation $P(r,r_l)$ due to an absorbing point object at a position $r_l$ within the turbid medium gives rise to a change in photon density at a position r given by $$P(r,r_l) = \frac{\exp[-K(|r_l-r_s|+|r_l-r|-|r-r_s|)]}{|r_l-r_s||r_l-r|/|r-r_s|} \tag{4}$$

Figure 2:
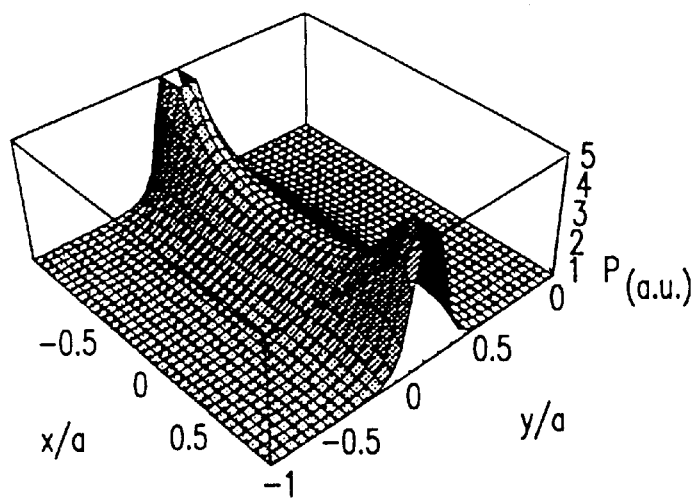
FIG. 2 shows a surface of a perturbation function.

FIG. 2 shows a surface plot of the functional form of said perturbation function. In the perturbation function shown in FIG. 2, the source and detector position of a first source/detector pair are assumed to be, for example, at the positions $r_s=(-\alpha,0,0)$ and $r_d(\alpha,0,0)$, respectively. The plot is given only for the z=0 plane. The units in the plots are normalized by dividing the value of the position in the x direction and the y-direction by the value a of the position of the source and the detector. The units in the z-direction are arbitrary units. The actual three-dimensional shape can be obtained by rotating the shape around the x-axis. The meaning of the perturbation function P can be expressed as the difference between a photon fluence measurement and an expected value of the photon fluence, according to this function the cause of this difference can be attributed to any point in the object space.

In order to find an expression for said difference it is assumed that an intensity measurement is made at a detector position $r_d$. Using the source and detector positions $r_s,r_d$ a value of the perturbation $P(r_d,r_l)$ is calculated to assign a strength value to the object space. A possible distribution $q(r_l)$ is thus obtained for all possible $r_l$ within the object space. For simplicity, $q(r_l) \gg q(r)$ is assumed and the strength q is then expressed as $$q(r_l) = \frac{1}{P(r_s,r_d,r_l)}\left[1 - \frac{\phi(r_d)}{\phi_0(r_d)}\right] \tag{5}$$

or $$q(r_l) = \frac{1}{P(r_s,r_d,r_l)} \frac{\phi_0(r_d)-\phi(r_d)}{\phi_0(r_d)} = W(r_s,r_d,r_l) \frac{\Delta\phi(r_d)}{\phi_0(r_d)} \tag{6}$$

wherein the difference between the measured and the expected value of the transmitted intensity is $\Delta\phi_{r_d}=\phi_O(r_d)-\phi(r_d)$ and the weighting function (in m) is $$W(r_s,r_d,r_l) = \frac{1}{P(r_s,r_d,r_l)} = \frac{|r_l-r_s||r_l-r_d|/|r_d-r_s|}{\exp[-K(|r_l-r_s|+|r_s-r_d|-|r_d-r_s|)]} \tag{7}$$

Figure 3:
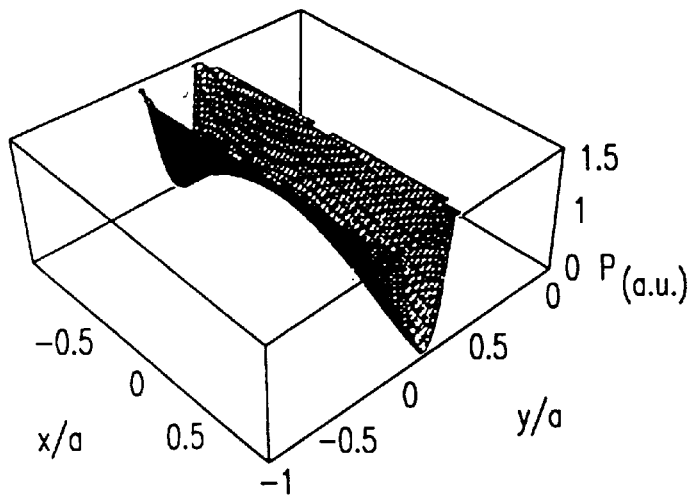
FIG. 3 shows a weighting function.
Figure 4:
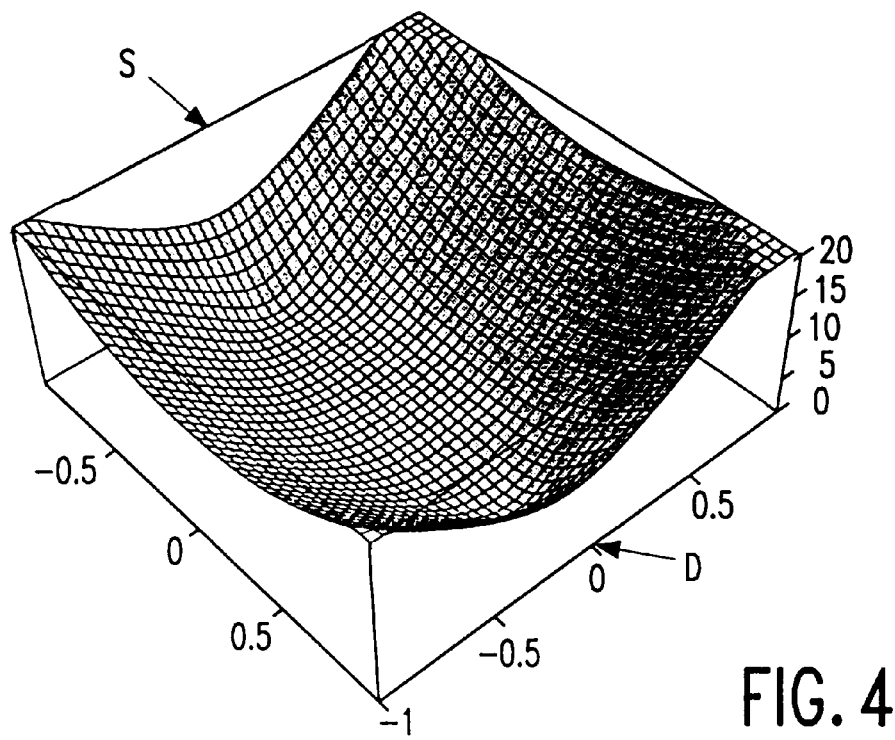
FIG. 4 shows a weighting function for a source/detector pair directed in the Y-direction.

The plot of the weighting function W is given in FIG. 3, which shows the spatial dependency of the strength q(r) of a perturbation at each position r in the object space which could account for the measured intensity difference $\Delta\phi(r_d)$ at the detector position $r_d$. The parameters used in the plot of FIG. 4 are identical to those of FIG. 2, except that the strength q(r) is plotted on a logarithmic scale.

A further description of the transport of light via a turbid medium can be found, inter alia, in the cited article "Monte Carlo Simulations of Photon Migration Path distributions in Multiple Scattering Media", by S. Feng et al, SPIE, Vol 1888, 1993, page 78–89.

Figure 5:
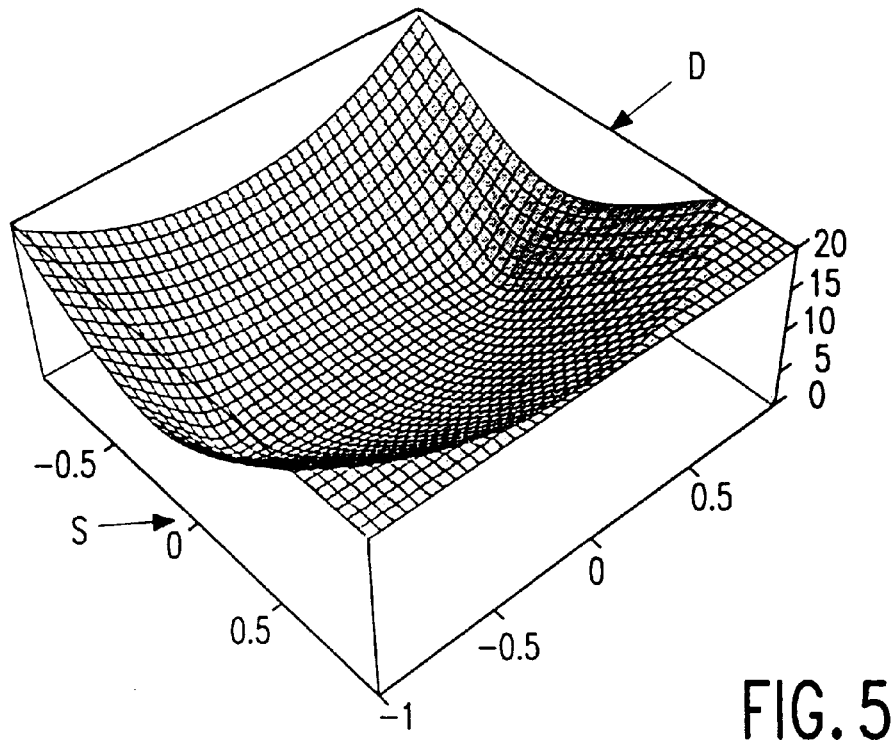
FIG. 5 shows a weighting function for a source/detector pair directed in the X-direction.
Figure 6:
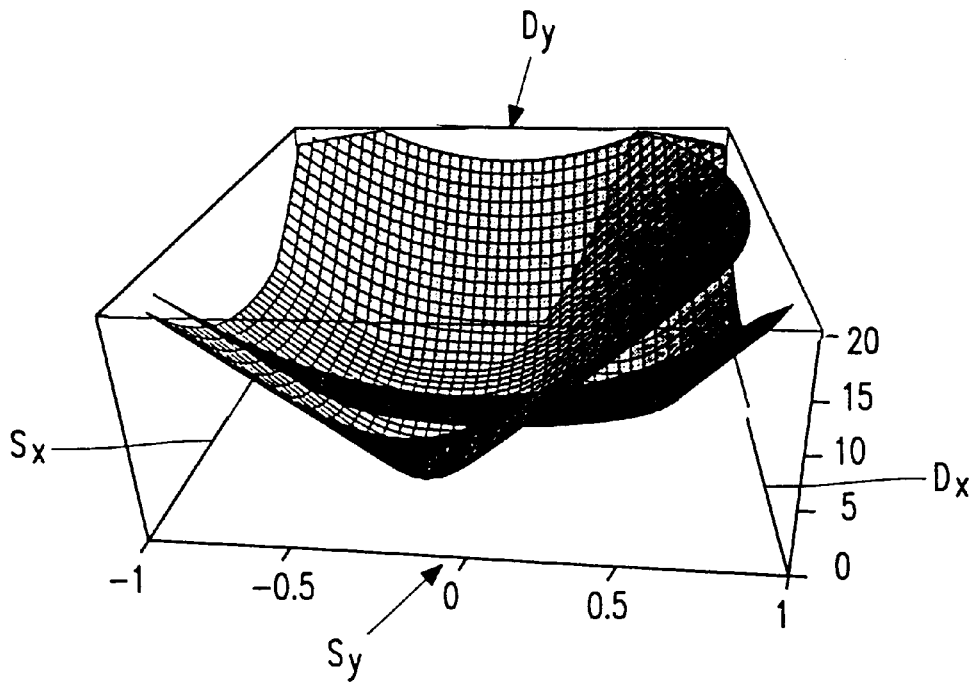
FIG. 6 shows an integrated plot for two weighting functions for different source/detector pairs.

In order to enable reconstruction of the turbid medium, weighting functions from different source/detector pairs are to be used. Therefore, a second light source/detector pair is considered, the source of said second light source/detector pair being located, for example, at position (0,a,0) and its detector at position (0,-a,0) in the normalized coordinate system. The source detector lines of the first and the second light source/detector pair are directed in the x-direction and the y-direction, respectively. The weighting functions $W_1,W_2$ of the first and the second light source/detector pairs are shown in FIGS. 4 and 5, respectively. The weighting function $W_2$ of the second source/detector pair is different from the weighting function $W_1$ of the first source/detector pair, as can be seen from FIGS. 4 and 5. However, the weighting functions $W_1$ $W_2$ are said to correlate where they agree on the existence of an object. This correlation can be found, for example, by plotting the surface plots of the weighting functions $W_1, W_2$ in the same plot. FIG. 5 uses also a logarithmic scale to plot the values of the weighting function. FIG. 6 shows the integrated plot of the two weighting functions $W_1, W_2$. In FIG. 6 the cross-section of the surfaces defines two lines where the weighting functions $W_1, W_2$ of both source/detector pairs correlate to assign their strength of perturbation to the object. The correlation can also be reproduced in a plot showing, for example, the difference between the weighting functions $W_1, W_2$ of the two source/detector pairs.

Figure 7:
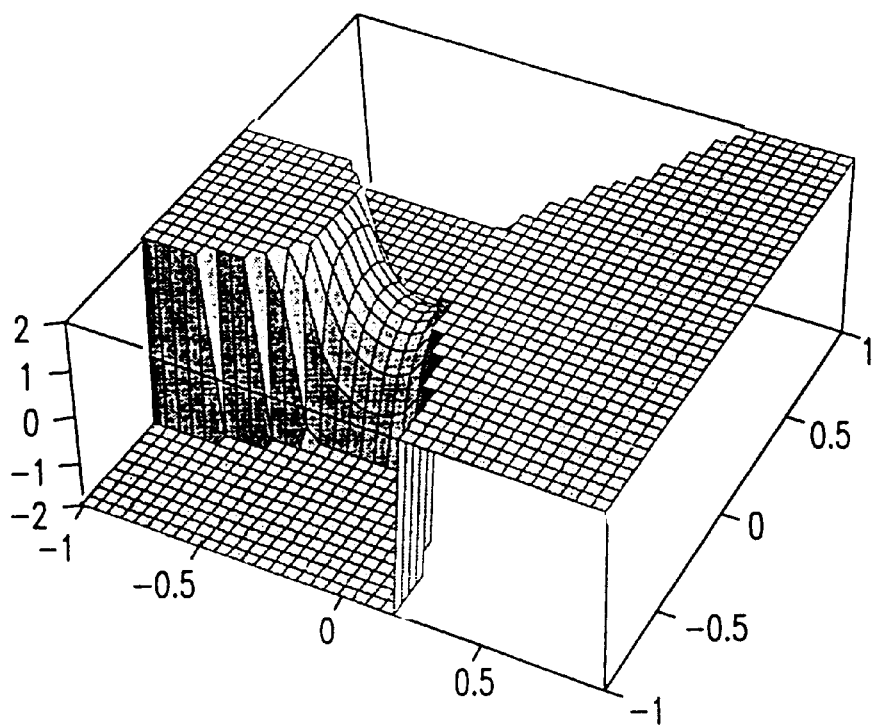
FIG. 7 shows a difference plot for two weighting functions for the different source/detector pairs.

FIG. 7 shows a difference plot of two weighting functions of the different source/detector pairs. For points of the image having a small correlation, i.e. point showing a large difference between the weighting functions $W_1, W_2$, FIG. 7 illustrates that there is no possible assignment for the existence of an object for that point. However, for points of the image having a high correlation, i.e. the difference between the weighting functions $W_1$, $W_2$ is small, zero or close to zero, and thus there is possible assignment for the existence of an object for that point. The possibility of finding the object is greater when this difference is closer to zero.

Figure 8:
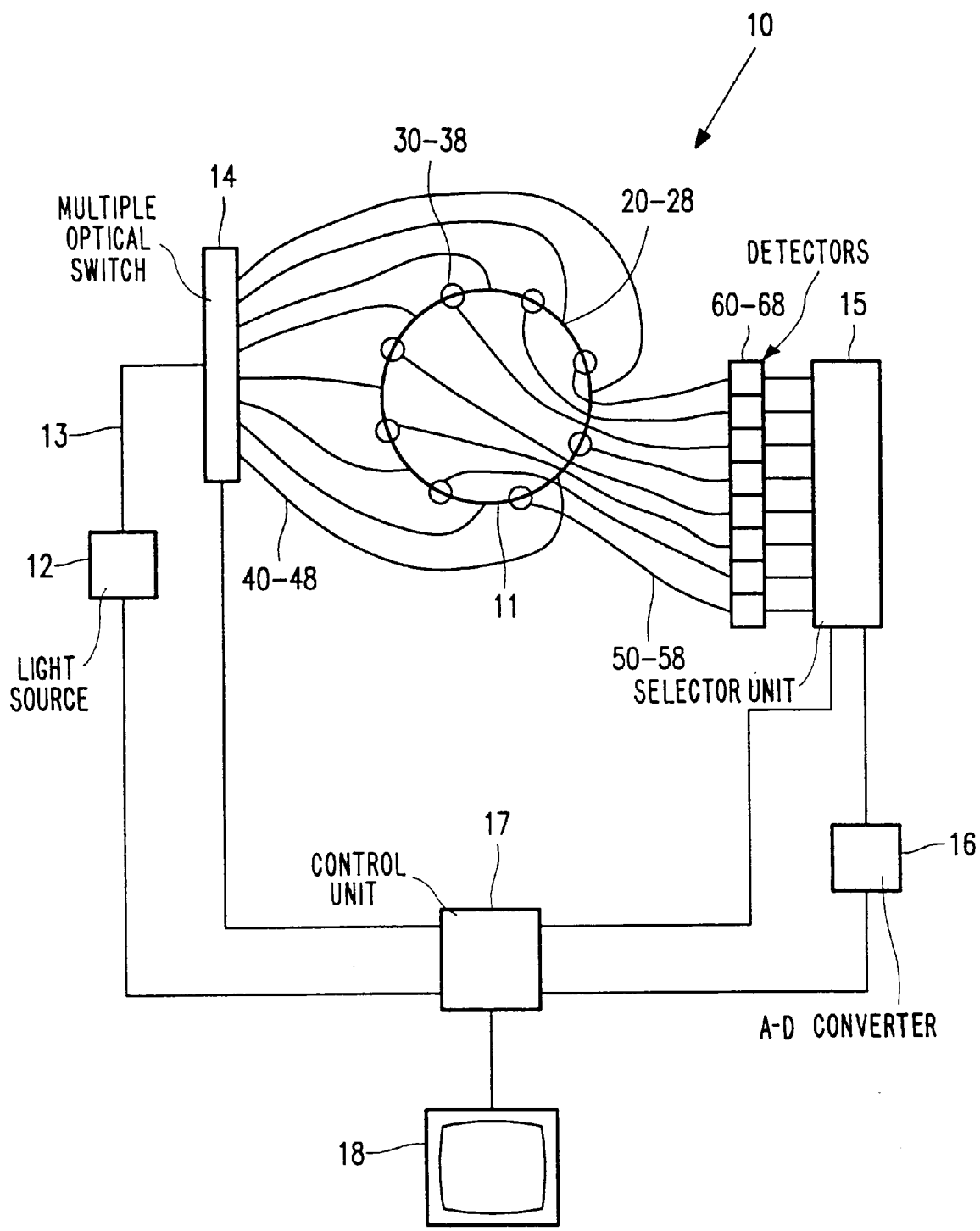
FIG. 8 shows an embodiment of a device according to the invention.

The localization of an object can be further improved by employing more source/detector pairs that have to correlate on the weighting functions to assign an object to a point, as is illustrated by FIG. 8.

FIG. 8 shows an embodiment of a device according to the invention, in this case being a mammography device 10. Even though the device in accordance with the invention is described, by way of example, for a mammography system, it can likely be used also for the examination of other parts of a human or animal body. The present device is intended to detect inhomogeneities in the tissue of a female breast. Examples of such inhomogeneities are increased microvascularizations or a high concentration of small blood vessels around a malignant tumor. The device in accordance with the invention is arranged to image such anomalies when they are still very small, so that a carcinoma can be discovered at an early stage, however, without subjecting the patient to the risks of examination by means of ionizing radiation, such as X-rays.

The device 10 comprises a plurality N of measuring light sources 20–28, inserted at positions $r_i$ (j=1, . . . ,N) into the wall of a cup 11 and a plurality N of detectors 30–38 inserted at position $r_j$ (j=1, . . . ,M) into the wall of the cup. N and M are a fixed numbers, for example, in the range between 64 and 256. In practice these numbers are 256 for both N and M. In FIG. 8 the numbers of sources and the numbers of the detector are assumed to be eight for the sake of simplicity. Furthermore, FIG. 8 shows a light source 12, for example, a semi-conductor laser, which is optically connected, via a first optical waveguide 13, to an input of a multiple optical switch 14, the outputs of which are connected to a first plurality of second optical waveguides 40–48. The exit windows of the second optical waveguides form the measuring light sources 20–28 at the positions $r_i$. The detectors 30–38 inserted into the wall of the cup 11 are formed by entrance windows at positions $r_j$ of a second plurality of third optical waveguides 50–58, the exit windows of which are optically coupled to M detectors 60–68. The optical waveguides are, for example, optical fibres. The detectors 60–68 comprise, for example, PIN photodiodes. The outputs of the detectors 60–68 are electrically coupled to the inputs of a selector unit 15. An output of the selector unit 15 is coupled to an analoge-to-digital converter 16. The output of the A–D converter is coupled to a control unit, for example a micro-computer 17. The micro-computer 17 controls the light source 12, the multiple optical switch 14, the selector unit 15 and the A–D converter 16.

In order to reconstruct the interior of a turbid medium arranged within the cup 11, for example, a part of the breast of a human female, the control unit 17 is arranged to perform intensity measurements for every source/detector pair. Subsequently, the control unit performs a reconstruction method to reconstruct an image of the interior of the part of the breast within the cup. A monitor 18 displays the reconstructed image.

Figure 10:
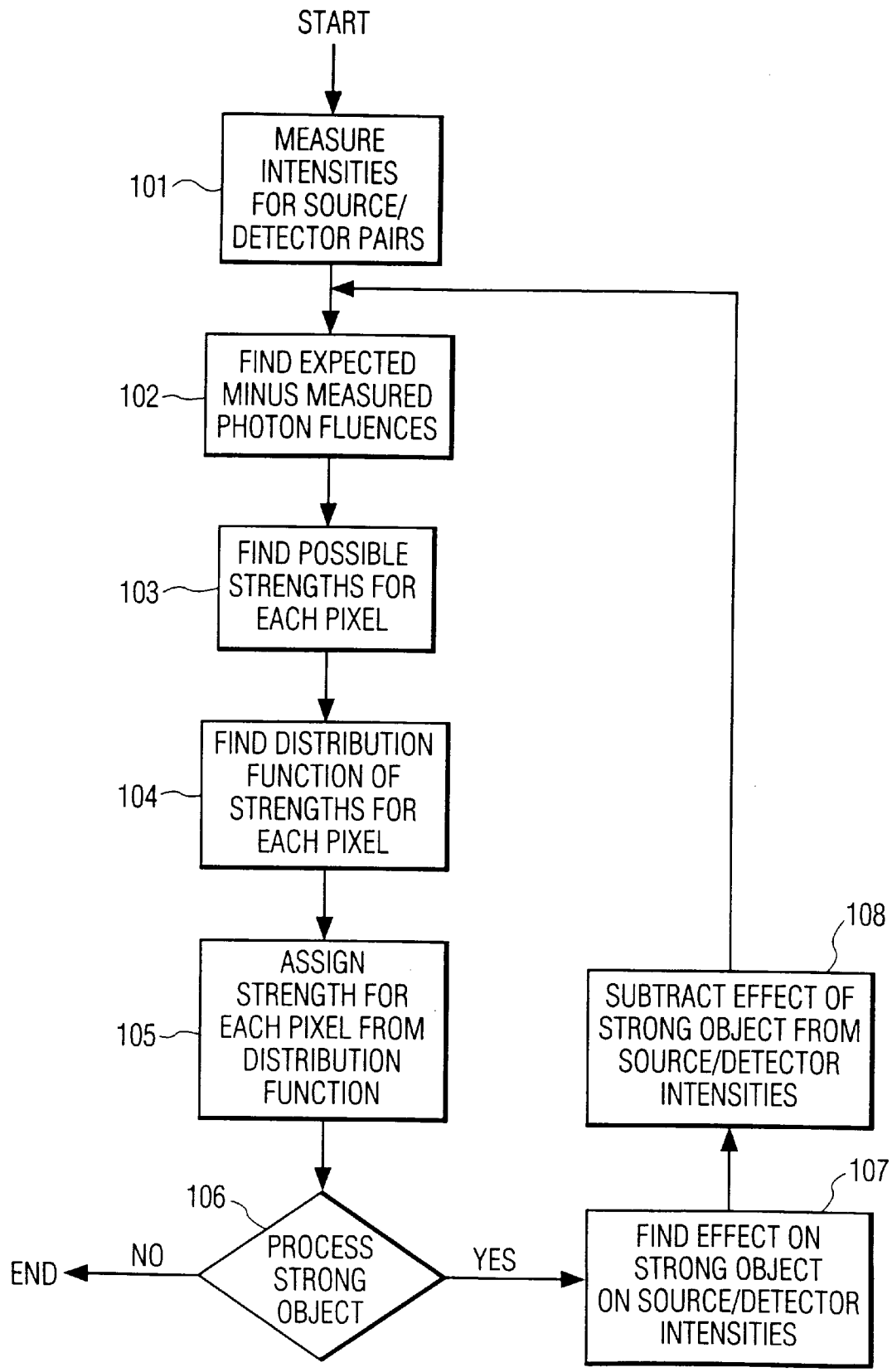

In a first step (101 in FIG. 10.) of the reconstruction method according to the invention the intensities from each source/detector pair (i,j) are measured. These intensities are stored in an (M×N) array. In a further step (102) the differences are calculated between the expected value of the photon fluence and the measured value of the photon fluence as $\Delta\phi(r_d) = \Phi_O(r_d) - \phi(r_d)$, wherein $\Phi(k,r_i,r_j)$ is calculated from the formula $$I(r_i, r_j) = A_0 \phi(r_i, r_j) \frac{S_0 A_0}{4\pi D'} \frac{\exp[-K|r_j - r_i|]}{|r_j - r_i|}.$$

$\phi_O(r_i,r_j)$ is the expected detector value for a source/detector pair (i,j) as given by the formula (1). Another possibility is to employ instead of a calculated expected photon fluence an estimated value of the expected photon fluence, for example, the average value of the measured values of the photon fluences.

In a next step (103) of the method for each pixel k of an image to be reconstructed there are calculateed the possible strengths q(k,i,j) for each of the source/detector pairs i,j. The possible strength $q(k,r_i,r_j)$ assignable to each pixel k is then calculated using formula (6) and is expressed by formula $$q_{(k,i,j)} = W(k, r_i, r_j) \frac{\Delta\phi(i, j)}{\phi_0(i, j)},$$

wherein $W(k,r_i,r_j)$ is the weighting function given by formula (7).

In a next step (104) a distribution function of the possible strengths assignable to each pixel to be reconstructed is determined. The distribution function comprises a plurality of histograms, i.e. one histogram for each pixel k. Each bin of the histogram represents a value of the possible strength and the frequency of the bin represents the occurrence of possible strengths determined for each pixel for all differences determined. A correlation between the possible values of the strength is then assumed for the maximum frequency of the histogram. The value of the bin of the maximum frequency is then assigned (step 105) as the value of strength $q_k$ to the corresponding pixel k. As a result a strong object appears non-blurred in the reconstructed image. Furthermore, it is an advantage of said method that it enables three-dimensional imaging, because the reconstruction of an image is not limited to inhomogeneities in a source detector plane only; employing the weighting function accounts also for inhomogenities beyond the source detector plane.

It is also possible to correct this strength q(k) for each pixel k for the standard deviation $\sigma_k$ of the histogram by multiplication of the value assigned by a correction factor defined by $$\frac{1}{1 + a\sigma_k},$$

wherein $\sigma_k$ is the standard deviation of the histogram of the pixel and a is a constant determined by the desired bit accuracy of the image as $$a = \frac{2^b}{q_{\max}},$$

wherein b represents the bit accuracy and $q_{max}$ is the maximum value of the weighting function. The bit accuracy has a value of, for example, 8 bits. The effect of this step is that the strength of the pixel is corrected for the standard deviation of the histogram. For a high standard deviation $\sigma_k$ only a small value of the strength will be assigned to the pixel. For a low standard deviation $\sigma_k$ the histogram is peaked around a central value and that central value will be assigned to the pixel.

In a further method according to the invention one or more iteration steps can be executed. In that iteration step (107 in FIG. 10) the strength value $q_k$ assigned to each pixel k of a strong object is employed to calculate the effect on the intensity for each source/detector pair (i,j). The intensity at the position of a detector j of the source/detector pair (i,j) is then given by $I = A_O \Phi(r_d) = A_O \Phi_O(r_d)[1 - q_k P(r_t, r_s, r_d)]$, wherein $A_O$ (in cm²) is a collection area of the input window of the detector j, $q_k$ represents the strength q of the perturbation assigned to the pixel k, and $\Phi_O(r_d)$ is defined as $$\frac{S_0}{4\pi D} \frac{\exp[-K|r_d - r_s|]}{|r_d - r_s|}$$

in which $S_o$ represents the initial source intensity and $$D = \frac{1}{3(\mu'_s + \mu_a)}$$

represents the normalized photon diffusion coefficient. By subtracting (step 108) the effect of the strong object from the intensities measured and by repeating said steps of the image reconstruction process an image is obtained in which smaller objects are deblurred. Furthermore, the image can be refined by a small number of these iterations, for example 3 to 5 times. As a result more small objects become visible in the resultant image.

Figure 9:
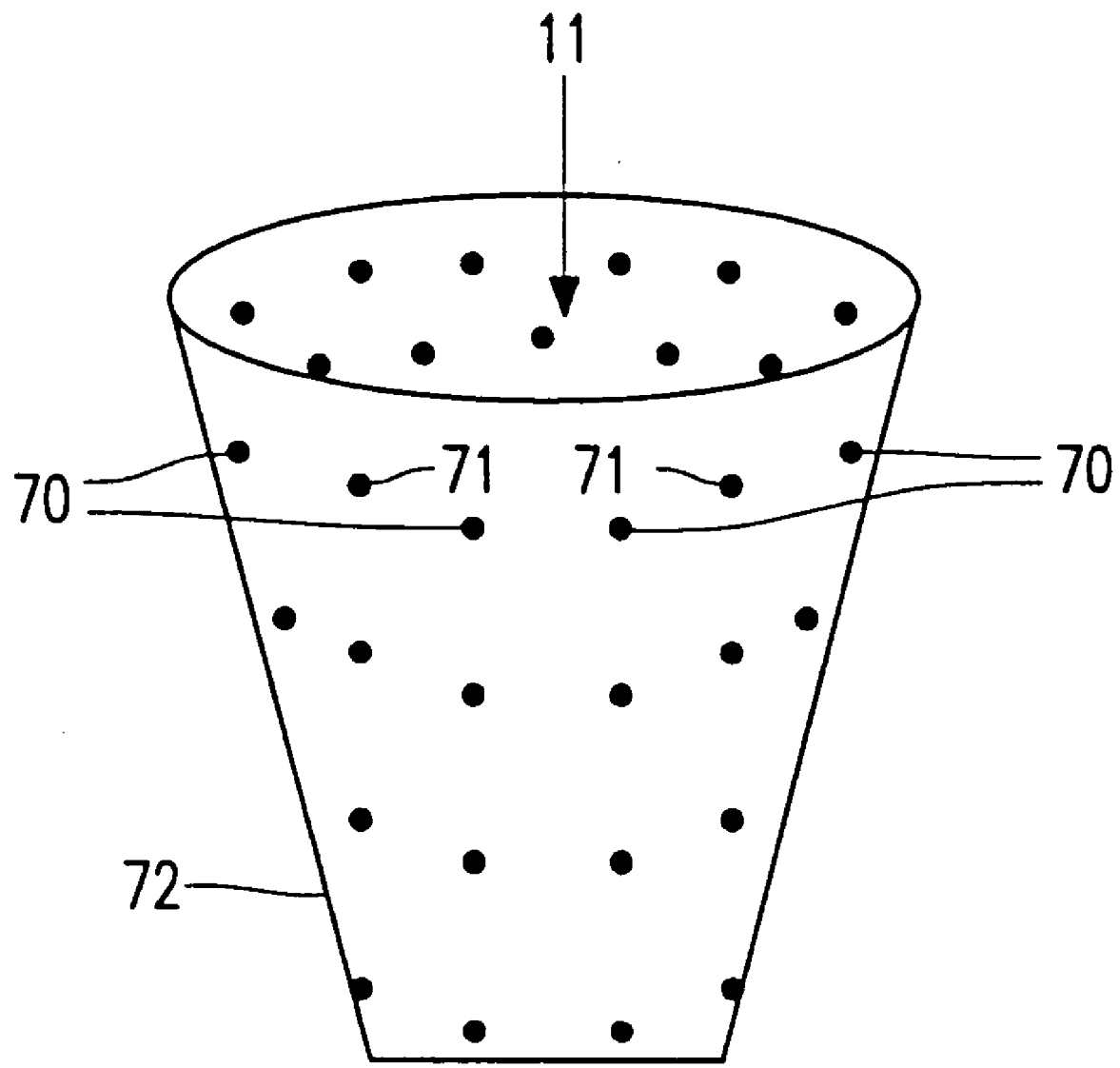
FIG. 9 shows a cup for holding a turbid medium, and FIG. 10 show an embodiment of methods according to the invention.

FIG. 9 shows an arrangement of the light sources and detectors around the cup 11. The light sources 70 and detectors 71 are inserted into the wall 72 at substantially uniformly distributed positions. Furthermore, the interior of the cup 11 is conceived to recieve for example, a part of a female breast.

I claim:

1. A method of imaging an interior of a turbid medium, in which method the following steps are performed:
    a) irradiation of the turbid medium with light of constant intensity and measurement of the constant intensities of light propagated along a plurality of light paths through the turbid medium, and
    b) determination of an image of the interior of the turbid medium from the constant intensities measured, characterized in that the following sub-steps are carried out for determining the image of the object:
        c) determination of differences between expected photon fluences and measured photon fluences from the constant intensities measured,
        d) determination of possible strengths assignable to each pixel of the image from combinations of weighting functions and the photon fluence differences determined,
        e) determination of a distribution function of the possible strengths assignable to each pixel, and
        f) determination of an image from the determined distribution function.

2. A method as claimed in claim 1, characterized in that the method also includes the following steps:
    determining the effects on the measured constant intensities due to one or more strong objects determined to be in the image,
    subtracting the determined effects from the constant intensities measured, and
    repeating steps c) to f).

3. A method as claimed in claim 1, characterized in that the distribution function comprises a histogram for each pixel, in which histograms each bin represents a value of the possible strength determined for a pixel and the frequency of the bin represents the occurrence of the possible strengths determined.

4. A method as claimed in claim 3, characterized in that for each pixel the value of the bin belonging to maximum frequency of the histogram of the pixel is assigned to the pixel.

5. A method as claimed in to claim 4, characterized in that for each pixel the pixel value assigned is multiplied by a correction factor $$\frac{1}{1 + a\sigma_k},$$

wherein $\sigma_k$ is the standard deviation of the histogram of the pixel and a is a constant determined by the desired bit accuracy of the image as $$a = \frac{2^b}{q_{\max}},$$

wherein b represents the bit accuracy and $q_{max}$ is the maximum value of the weighting function.

6. A method as claimed in claim 2, characterized in that the distribution function comprises a histogram for each pixel, in which histograms each bin represents a value of the possible strength determined for a pixel and the frequency of the bin represents the occurrence of the possible strengths determined.

7. A method as claimed in claim 6, characterized in that for each pixel the value of the bin belonging to maximum frequency of the histogram of the pixel is assigned to the pixel.

8. A method as claimed in to claim 7, characterized in that for each pixel the pixel value assigned is multiplied by a correction factor $$\frac{1}{1 + a\sigma_k},$$

wherein $\sigma_k$ is the standard deviation of the histogram of the pixel and a is a constant determined by the desired bit accuracy of the image as $$a = \frac{2^b}{q_{\max}},$$

wherein b represents the bit accuracy and $q_{max}$ is the maximum value of the weighting function.

9. A device for imaging an interior of a turbid medium comprising:
    a plurality of light sources for irradiating the turbid medium with light of constant intensity at a plurality of different source positions,
    a plurality of light detectors for measuring the constant intensities of light propagated through the turbid medium at a plurality of different detector positions,
    means for controlling said plurality of light sources and said plurality of light detectors for measuring the constant intensities of propagated light for combinations of the different source positions and the different detector positions, and
    means for reconstructing an image of the interior of the turbid medium by (I) determining differences between expected photon fluences and measured photon fluences from the constant intensities measured, (ii) determining possible strengths assignable to each pixel of the image from combinations of weighting functions and the determined photon fluence differences, (iii) determining a distribution function of possible strengths assignable to each pixel of the image, and (iv) determining an image from the determined distribution function.

10. The device of claim 9 wherein said means for controlling and said means for reconstructing comprise a computer.

11. The device of claim 9 further comprising a display device for displaying the reconstructed image.

12. The device of claim 9 wherein the means for reconstructing further comprises determining effects on the measured intensities due to one or more strong objects determined to be in the image, subtracting the determined effects on the intensities from the measured constant intensities, and repeating steps (I) to (iv).

* * * * *